United States Patent [19]

Gulley, Jr.

[11] 4,150,291
[45] Apr. 17, 1979

[54] NONDESTRUCTIVE TESTER FOR FIBERGLASS-ALUMINUM HONEYCOMB STRUCTURES

[75] Inventor: Lee R. Gulley, Jr., Dayton, Ohio

[73] Assignee: The United States of America as represented by the Secretary of the Air Force, Washington, D.C.

[21] Appl. No.: 864,067

[22] Filed: Dec. 23, 1977

[51] Int. Cl.² .......................................... H01T 19/04
[52] U.S. Cl. .................................................. 250/324
[58] Field of Search ...................... 250/324, 325, 326; 324/32, 215, 216; 361/235

[56] References Cited

U.S. PATENT DOCUMENTS 3,344,345  9/1967  Molina ................................. 324/215
3,351,760  11/1967  Brown ................................. 324/216

*Primary Examiner*—Bruce C. Anderson
*Attorney, Agent, or Firm*—Joseph E. Rusz; Robert K. Duncan

[57] ABSTRACT

Defects and irregularities in fiberglass-aluminum honeycomb structures are visually displayed by ionization corona formed by a relatively high potential on a conductive mesh screen contained in transparent dielectric hand-held probe. Both the frequency and the amplitude of the potential are controllable by hand operated controls on the probe to provide optimum electrographic images in the ionization of the air in the interelectrode gap between the probe electrode and the structure being examined.

4 Claims, 5 Drawing Figures

NONDESTRUCTIVE TESTER FOR FIBERGLASS-ALUMINUM HONEYCOMB STRUCTURES

RIGHTS OF THE GOVERNMENT

The invention described herein may be manufactured or used by or for the government of the United States for all governmental purposes without the payment of any royalty.

BACKGROUND OF THE INVENTION

The field of the invention is in the nondestructive testing art and more particularly in the art of nondestructive testing of fiberglass-aluminum honeycomb structures.

There are many well known machines for nondestructive testing of structures. Some of the better known are atomic particle radiation systems, X-rays devices, sonic devices, permeability measuring devices, and various resistive and capacitive devices. Many of the prior art devices are laboratory instruments, few are portable enough to permit testing of structures in the field.

In many instances it is highly desirable to expediently test or examine assembled fiberglass-aluminum honeycomb structures such as helicopter blades and other similar aircraft structures for the presence of entrapped water, moisture, foreign fluids, and vapors which could cause a future failure of the structure. The present invention is particularly well suited for the foregoing. The best known prior art of interest in the background of the present invention is contained in the following patents. U.S. Pat. No. 2,831,123 to patentee Webster J. Daly; U.S. Pat. No., 3,237,068 to patentee Milton M. Sowiak; U.S. Pat. No. 3,351,760 to patentee R. L. Brown; and U.S. Pat. No. 3,809,974 to patentees R. A. Grange et al.

SUMMARY OF THE INVENTION

The invention provides a lightweight portable, hand-held viewing probe for the rapid testing of fiberglass-aluminum honeycomb structures, either of flat or moderated curvature, for anomalies and entrapped foreign substances. The portable probe eliminates the need to remove the structure under test from its attachments. The probe can be easily held overhead by the technician providing a rapid scanning of otherwise difficult areas.

DESCRIPTION OF THE PREFERRED EMBODIMENT

Figure 1:
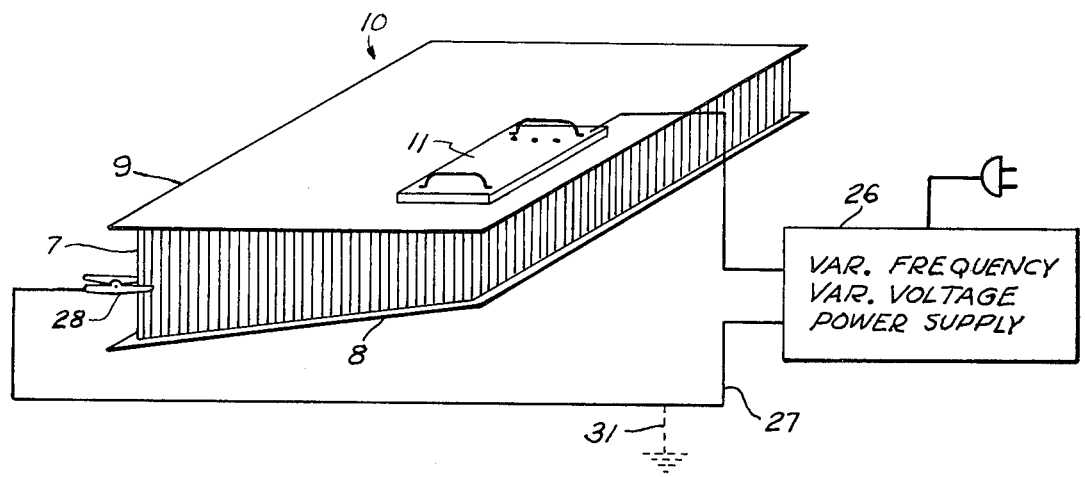
FIG. 1 pictorially illustrates a typical application of the invention.
Figure 2:
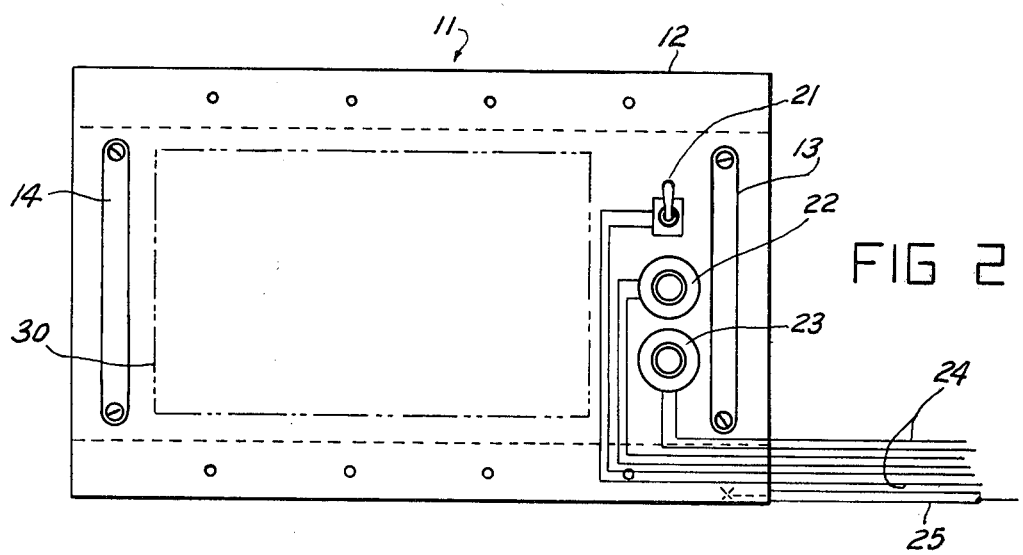
FIG. 2 pictorially illustrates a top view of a typical embodiment of the invention.

Referring to FIGS. 1 and 2, the probe 11 is positioned adjacent the fiberglass-aluminum honeycomb structure 10, which it is desired to examine for flaws. Generally, the aluminum honeycomb 7 is supported between fiberglass skin members 8 and 9. The skin may or may not be painted. High voltage or electrographic imaging results from the ionization of air in the interelectrode gap between the electrodes formed by conductor of the part being tested and the probe electrode. A dielectric positioned between the two electrodes allows some control over the ionization and provides visual or film observation of the result. In the embodiment of the probe described in detail, a clear acrylic sheet is the preferred dielectric which provides instantaneous, continuous viewing of the electrical picture caused by the ionization. Likewise, the probe electrode is also semi-transparent (typically a copper mesh screen) or, if desired, it may be made almost completely transparent by using a conductive coated (on one side) piece of clear glass plate. This further facilitates easy instantaneous viewing. Using a variable voltage, and variable frequency power supply to supply the ionization results in the ability to fine tune images of different materials that would be impossible to do if either of those two variables were a constant.

The fabrication and operation of a specific embodiment of the invention will be described in detail. While generally this embodiment set forth in detail is considered the optimum structure for a hand-held, one man operation, embodiment of the invention, it is to be understood that this specific embodiment is set forth by way of example and not to be considered limiting to the scope of the invention which is delineated by the appended claims.

Figure 3:
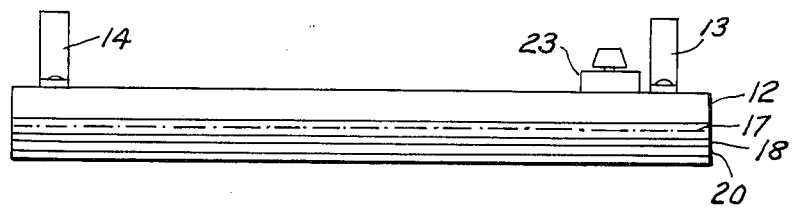
FIG. 3 schematically illustrates the front view of the probe shown in FIG. 2.
Figure 4:
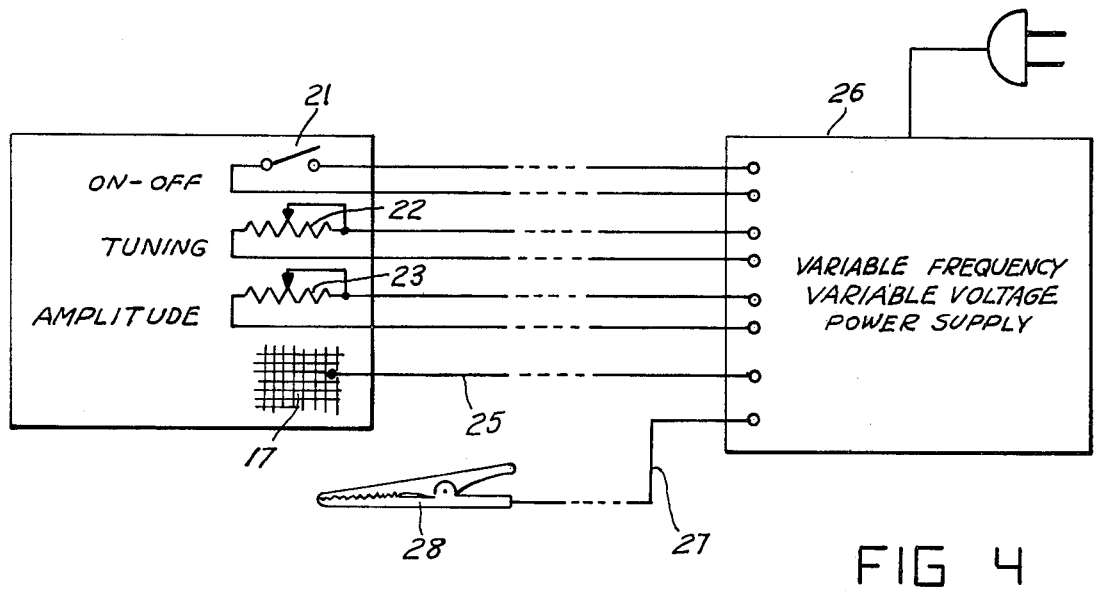
FIG. 4 is a block-schematic diagram of a typical electrical circuit of the invention.
Figure 5:
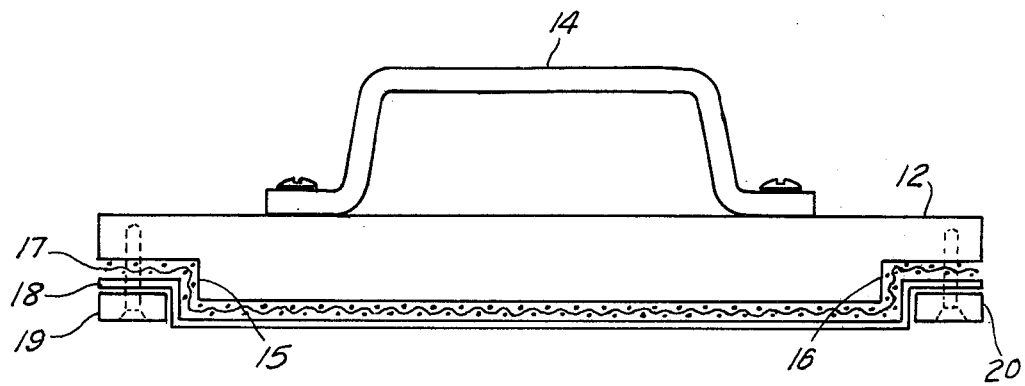
FIG. 5 is a schematic-pictorial end view of a typical embodiment of the invention.

In this preferred hand-held embodiment of the invention the probe comprises of a piece of clear acrylic plastic 12 approximately $7/16 \times 8 \times 11$ inches with two handles 13 and 14 attached on each end (see also FIGS. 3 and 5). Steps 15 and 16, 3/16 inch deep, are cut along either side of the probe along its length. The steps are approximately $1 \times 11$ inches in size. An $8 \times 11$ inch copper wire mesh screen 17 ($20 \times 20$ screen squares/inch) covers the complete face of the acrylic probe on the side opposite the handles. This mesh electrode and a sheet of clear acetate 18 are attached to the probe using two strips of aluminum 19 and 20 or other suitable material. The strips fit flush within the steps on either side of the probe and are held to the insulative probe member 12 by small countersunk screws.

On the upper surface of the probe near the right handle 13, an "on-off" toggle switch 21 and two conventional 10K $\Omega$ potentiometers 22 and 23 are attached for control of the excitation frequency and voltage. These are conventionally attached with screws into the acrylic plastic member 12. The wires from each control and the switch are run in a bundle 24 to the power supply remotely located. An additional high voltage wire 25 is run from the edge of the copper wire mesh to the high voltage terminal on the power supply. The high voltage wire should preferably be soldered to the copper mesh. Each connecting wire is standard stranded copper with flexible plastic insulation.

The conventional power supply 26 produces a variable voltage, variable frequency output from a solid state AC generator. The voltage is tunable from 3 to 42 KHz with an output range of 0 to 10 (nominal) Kilovolts. Output is in a continuous sine wave format. A suitable commercially available power supply for this embodiment is the Edmund Scientific Co., Barrington, N.J., Model No. 72,053. In this particular power supply tuning and amplitude are both controlled by 10K potentiometers. It is to be understood that other power supplies having other conventional means for controlling frequency and amplitude may equally well be used with the invention.

Activation of the power supply with the probe in place causes a "skin effect" current to flow mainly on the surface of a test part. Light is emitted by the subsequent corona discharge. The discharge is modulated by features of the test specimen, some of which are indicative of flaws or anomalies such as the presence of moisture. The generally effective viewing area 30 of this embodiment is approximately five inches by seven inches.

With the probe attached to the power supply as shown in the drawings, the unit is switched on by the remote on-off toggle switch 21. This activates the power supply 26. At this point, the probe is typically placed approximately within 1/16 of an inch from the surface of the part to be tested which has been grounded with a suitable ground wire 27 (stranded copper with flexible plastic insulation). In the case of aluminum honeycomb/fiberglass skin components, the aluminum core 7 is grounded to the power supply ground by use of the ground wire 27 with an alligator style clip 28. A physical earth ground 31 is generally desirable although not required. Ideally, and when convenient, the probe is placed beneath the part so that any water within the cells is held by gravity against the fiberglass skin. (The power supply is pre-set to the continuous wave mode of operation). Best operation is generally obtained when the area surrounding the probe and viewer's head is darkened or when not over 4–5 foot candles of ambient light is present. The 10K Ω voltage and frequency control potentiometers are then alternately increased from a zero reading slowly until a bluish corona is produced on the surface of the test part, viewed through the clear acrylic sheet. At this point the controls are then adjusted very carefully to provide the optimum image of the core internal structure. Care must be taken to prevent the use of excessive voltage which may burn through the relatively thin acrylic plastic dielectric.

Those cells within the structure containing water or possibly a particular gas, will have bright interiors whereas the other cells containing no water or possibly gases will appear dark. Cell sizes on the order of ⅛" to ¼" in diameter have been easily imaged with the unit being described in detail. The lower limit of the cell size to be imaged is generally limited by mesh size of the screen electrode. This lower limit has been greatly extended in some embodiments by utilizing a glass electrode having a thin film of gold deposited on its surface. The thin film of gold is thin enough to be nearly transparent yet it is thick enough to conduct electrical current and acts as one of the two electrodes.

With the embodiment illustrated in the drawing, water levels as small as one milliliter have been detected in conventional honeycomb cells.

Fiberglass skin thickness through which images have easily been seen are approximately 0.008 inch or slightly greater. Typical surfaces were coated with a gray standard aircraft primer and lacquer. It appears that thicknesses up to 0.125 inches can be penetrated.

Utilization of the equipment, particularly in the continuous wave mode, produces ozone gas in amounts large enough to cause some dizzyness in a nonventilated room, within several minutes. Caution should be exercised to insure a moderate air flow to prevent ozone buildup and also the infiltration of any explosive vapors.

It has been noted that a conductive gas or water vapor was detected while inspecting a boron/aluminum core/fiberglass structure. The reason for its being identified as a gas is that upon drilling holes in those cells containing the bright indications, the indications immediately vanished thus indicating the probable release of a gas to the atmosphere.

The probe may also be used to detect missing or disbonded and crushed core within fiberglass aluminum honeycomb structures. Lack of strong corona in the area of several cells indicates a separated, short core which is considered as detrimental a defect as is water within the cells. Missing core or corroded core likewise is a problem, and with skill, it is generally detectable with the probe.

The probe also has proven successful in the detection of surface changes on aluminum sheet. It has been found that when the probe is placed over a non-oxidized (clean) area that a much brighter corona existed than when placed over an oxidized area.

I claim:

1. A nondestructive testing probe for detecting flaws in fiberglass-aluminum honeycomb structures comprising:
   a. a transparent insulative probe member having an upper and a lower surface;
   b. a left-hand and a right-hand holding means positioned on the said upper surface;
   c. a semi-transparent probe electrode positioned on the said lower surface;
   d. a transparent dielectric material positioned over and covering the said electrode;
   e. means for providing an alternating potential between the said aluminum honeycomb and the said probe electrode; and
   f. means positioned on the said upper surface of the transparent insulative probe member for controlling the amplitude and frequency of the said alternating potential, whereby a corona discharge is formed between the said dielectric material and the said fiberglass-aluminum honeycomb structure providing in the said corona discharge a visual image of the said honeycomb structure.

2. The apparatus as claimed in claim 1 wherein the said means for controlling the said potential amplitude, controls the potential amplitude over a range of approximately zero volts to ten kilovolts, and the said means for controlling the said frequency of the said potential controls the frequency from approximately 3 KHz to approximately 42 KHz.

3. The apparatus as claimed in claim 2 wherein the said means for controlling the said amplitude and the said means for controlling the said frequency are positioned adjacent a said holding means.

4. The apparatus as claimed in claim 1 wherein the said means for providing an alternating potential between the said aluminum honeycomb and the said probe electrode includes a power supply having an alternating current output remotely controllable over a frequency range of approximately 3 KHz to 42 KHz and a potential controllable from zero to approximately 10 kilovolts cooperating with the said probe electrode, the said aluminum honeycomb and the said amplitude and frequency controls.

* * * * *